US007963957B2

(12) United States Patent
Tolmei

(10) Patent No.: US 7,963,957 B2
(45) Date of Patent: Jun. 21, 2011

(54) VISUAL INDICATOR FOR ELECTROSURGICAL INSTRUMENT FIELDS

(76) Inventor: Ron Tolmei, Concord, CA (US)

( * ) Notice: Subject to any disclaimer, the term of this patent is extended or adjusted under 35 U.S.C. 154(b) by 1412 days.

(21) Appl. No.: 11/449,962

(22) Filed: Jun. 9, 2006

(65) Prior Publication Data
US 2007/0287997 A1   Dec. 13, 2007

(51) Int. Cl.
*A61B 17/00* (2006.01)
(52) U.S. Cl. .............................. 606/1; 606/37; 128/908
(58) Field of Classification Search .......... 606/1, 37–45, 606/167, 170; 128/908; 604/22
See application file for complete search history.

(56) References Cited

U.S. PATENT DOCUMENTS 3,138,919 A * 6/1964 Deutsch ......................... 60/202
5,140,221 A * 8/1992 Ichinose ....................... 313/581
5,736,818 A * 4/1998 Ulczynski et al. ........ 315/111.21

* cited by examiner

*Primary Examiner* — Ahmed M Farah
(74) *Attorney, Agent, or Firm* — D. Benjamin Borson

(57) ABSTRACT

A device to visually indicate the presence of electric fields in electrosurgical apparatus, without the necessity of wiring or an electrical connection to the apparatus, to visually annunciate when an electrosurgical instrument is active is disclosed. This is to alert the operating surgeon, and observing personnel, that the device is operational to mitigate the possibility of anyone inadvertently being injured. The device is comprised of an electrically insulated enclosure filled with a gas in close proximity to a surgical handpiece connected to a radio frequency current generator.

11 Claims, 3 Drawing Sheets

VISUAL INDICATOR FOR ELECTROSURGICAL INSTRUMENT FIELDS

CROSS-REFERENCE TO RELATED APPLICATIONS

References Cited

U.S. Patent Documents

| | | | |
|---|---|---|---|
| 4,112,950 | Sep. 12, 1978 | Pike | 606/42 |
| 4,170,234 | Oct. 9, 1979 | Graham | 606/42 |
| 4,202,337 | May 13, 1980 | Hren, et al. | 606/48 |
| 4,347,842 | Sep. 7, 1982 | Beale | 604/20 |
| 4,427,006 | Jan. 24, 1984 | Nottke | 606/42 |
| 4,443,935 | Apr. 24, 1984 | Zamba, et al. | 29/622 |
| 4,545,375 | Oct. 8, 1985 | Cline | 606/42. |
| 5,817,091 | Oct. 6, 1998 | Nardella et al. | 606/38. |
| 6,242,741 | Jun. 5, 2001 | Eric Miller et al. | 250/363 |
| 6,402,741 | Jun. 11, 2002 | Keppel et al. | 606/34 |
| 6,534,770 | Mar. 18, 2003 | Miller et al. | 250/363 |
| 6,676,660 | Jan. 13, 2004 | Wampler et al. | 606/51 |
| 6,685,701 | Feb. 3, 2004 | Orszulak et al. | 606/34 |
| 6,984,826 | Jan. 10, 2006 | Miller et al. | 250/363 |
| 7,041,096 | May 9, 2006 | Malis et al. | 606/32 |

BACKGROUND OF THE INVENTION

1. Field of the Invention

The present invention relates to cost-effective and readily realizable means to reduce the possibility of unintentionally cutting or cauterizing a patient, or new born, in proximately of an electrosurgical handpiece.

2. Discussion of Background

The first documented case of cutting or cauterizing patients using electricity was in 1910 and later, in 1920, perfected by electrophysicist William Bovie and neurosurgeon Harvey Cushing when they collaborated in the development of modern electrosurgery.

Even though modern designs have improved capabilities they all essentially follow Bovie's initial design and the basic principle of operation has not changed.

That is, the vast majority of modern electrosurgical equipment today consists of a radio frequency current generator and handpiece that passes electrical current through tissue for the purpose of cutting or coagulating. It combines the principle of electricity and cautery in that it uses heat to destroy tissue or coagulate blood.

The handpiece is traditionally a passive pencil like device that is simply composed of a metal blade, switches that are used by the surgeon to select one of two modes of operation, a length of cable, and a connector to an electrosurgical generator that also renders replacement of the handpiece without wiring.

It is well documented in medical literature that on occasion electrosurgical handpieces fail and either self activate or are unable to become activated by the surgeon. Unfortunately these failures, if annunciated at all, are annunciated only on the remotely located generator and owing to background noise in the operating suite often not heard or seen by the surgeon. These self activating failures can and have caused patients to experience severe burns and in at least one occasion loss of an infant's toes during delivery. Further, when the handpiece fails to activate the surgeon's conditioned response is to try a different location on a patient, in an area removed from the surgical area, to test the handpiece. This trial and error approach causes unnecessary lesions in the patient.

Virtually all manufacturers of handpieces provide an insulated plastic holster that the surgeon is supposed to place the handpiece in, at bedside, whenever it is not in use and thereby avoid any possible contact with the patient. This has proved difficult because traditionally there is more than one surgeon attending the patient at any one time. Additionally, out of necessity the surgeons are located on opposite sides of the patient making it difficult to have a central location for the handpiece.

Recently a patent, by Allen et al. U.S. Pat. No. 6,986,768 B2, has been issued in an attempt to solve the problem by having a shield slide over the handpiece blade when the handpiece is not in use. This would mitigate, but not solve, the problem as it would require a surgeon to constantly slide the shield on and off—and that's probably not going to happen.

To date there have been numerous patents issued and suggestions submitted in an attempt to resolve the issue of failures associated with handpieces by various means. Some of these, as above, suggest implementation of physical obstacles while others attempt to provide a visual indication of operation on or in proximity to the handpiece. Unfortunately the vast majority of patents issued, notably by Nardella and Yates, U.S. Pat. No. 5,817,091, Miller, Rader, Wells and Stoppel, U.S. Pat. Nos. 6,534,770 B2 & 6,984,826 B2, Wampler, Yates, Speeg, Vaitekunas, Drake and Niezgoda U.S. Pat. No. 6,676,660 B2, Orszulak and Dobbins U.S. Pat. No. 6,685,701 B2 don't solve the problem. This is because the devices are: to complex, require wiring, require power, are expensive, not easily sterilized, are difficult to retrofit existing handpieces, physically interfere, and potentially interfere with the handpiece's electric field.

Without reservation, the most important issue in the implementation of any solution to this problem is its use and acceptance by surgeons.

Therefore as exemplified, the solution must be: cost effective, reliable, safe, not effect surgical procedures, compatible with existing technology and simple—all of which this present invention uniquely satisfies.

BRIEF SUMMARY OF THE INVENTION

Accordingly with the major aspects of the problem, already briefly recited, the present invention is a means to visually annunciate when an electrosurgical instrument is active. This is to alert the operating surgeon, and observing personnel, that the device is operational to mitigate the possibility of anyone inadvertently being injured. The device is comprised of an electrically insulated enclosure filled with a gas in close proximity to a surgical handpiece that is connected to a radio frequency current generator.

When the handpiece is activated the radio frequency (RF) current generator produces an electric field that is coupled to the handpiece. Because, by design, handpieces are nonconductors of electricity the electric field permeates the surrounding area and ionizes the gas contained in the nonconductive enclosure. The gas used in the enclosure is selected such that it will only ionize and fluoresce at wavelengths that are visible to the naked eye when in the presence of the electric field that is generated by the RF current generator.

In the preferred embodiment of the invention the nonconductive enclosure is made of glass, the gas is neon, and the entire assembly is imbedded into the handpiece as will be shown in the detailed description of the invention to follow.

Alternately the glass and gas assembly may be produced individually so that it can be adhered to a handpiece, or any other object, simply by peeling back its adhesive backing as will be shown in the detailed description of the invention to follow.

It is important to note that the main embodiment of the invention, the nonconductive enclosure containing gas, is available off-the-shelf technology and marketed as miniature Neon lamps.

Owing to the simplicity, cost, and elimination of any electrical connection with the handpiece this invention uniquely satisfies the shortcomings for previous patents.

Other features and their advantages will be apparent to those skilled in the art of designing cost-effective solutions to safety concerns for electrosurgical instruments from a careful reading of the Detailed Description of Preferred Embodiments accompanied by the following drawings.

DETAILED DESCRIPTION OF THE INVENTION

The present invention is a means to visually annunciate when an electrosurgical instrument is active by detecting the accompanying electric field and ionizing a gas filled lamp. This visual indication alerts surgeons, and bystanders, that the device is operational thereby mitigating the possibility of injuring a patient. The device is comprised of an electrically insulated enclosure filled with a gas in close proximity, but without electrical contact, to a surgical handpiece connected by cable to a radio frequency current generator.

Currently electrosurgical equipment have visual and audible annunciation when active but only on the radio frequency current generator that is usually located some distance away from the patients bed side. This makes it difficult to see or hear annunciations especially during procedures that require intense concentration.

This invention provides a visible indication that the device is active on the handpiece where the surgeon's attention is focused when performing surgery.

In addition, this invention uses technology that does not require any wiring or electrical contact with electrosurgical handpieces, is inexpensive, and can be used with existing electrosurgical equipment by simply attaching the device to the area of interest with sticky-back adhesive. Further, this invention capitalizes on response to visual stimuli from the point of patient contact with the surgical handpiece and therefore does not require visual reorientation that is distracting. For simplicity in this description handpiece is synonymous with electrosurgical equipment and the invention would operate with other surgical equipment in the same fashion as described.

Figure 1:
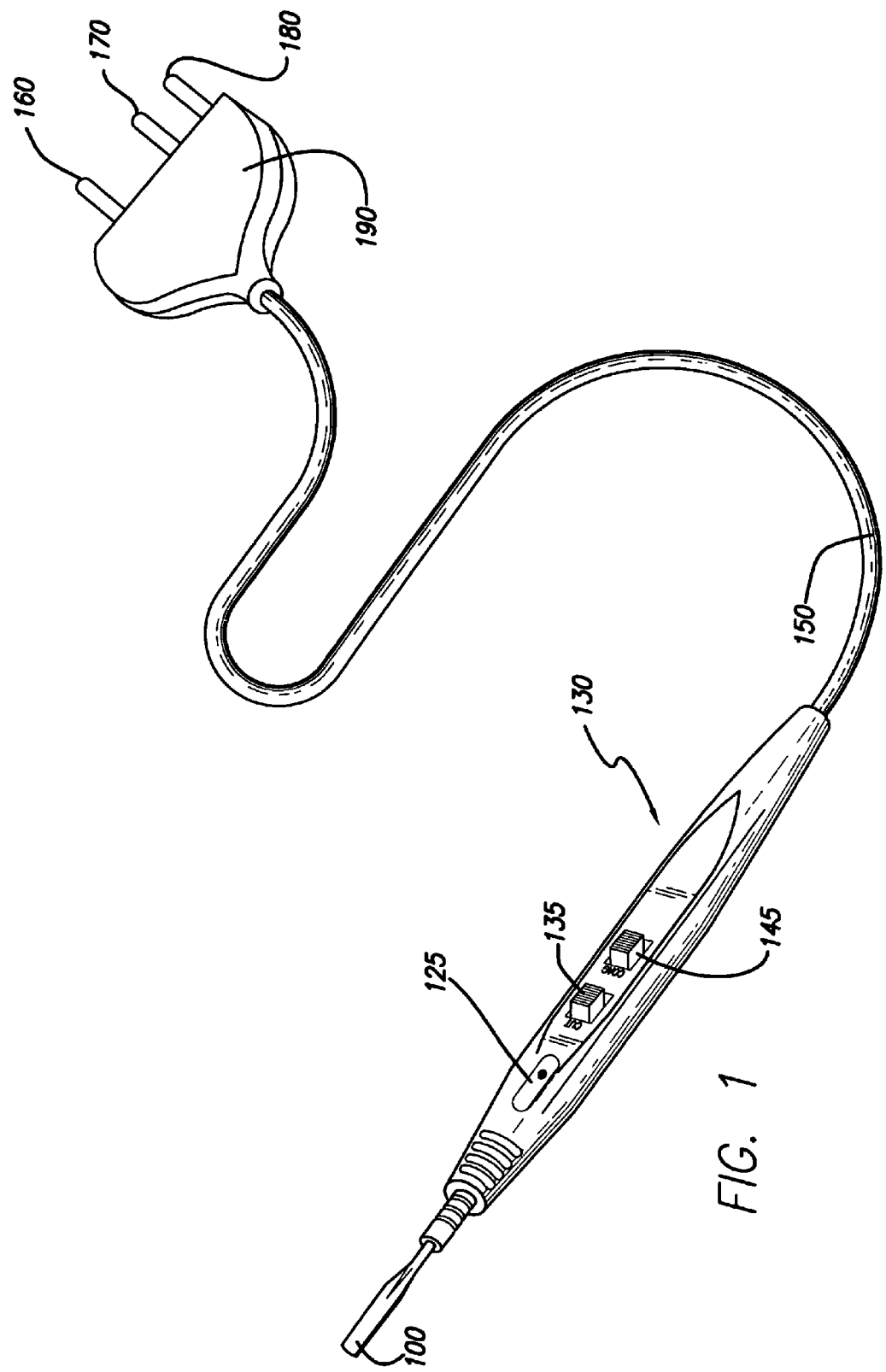
FIG. 1 is a pictorial of the preferred integral embodiment of the present invention to reduce the possibility of unintentionally cutting or cauterizing a patient, or new born, in proximately of an electrosurgical handpiece.

FIG. 1 is the preferred integral embodiment of the present invention to reduce the possibility of unintentionally cutting or cauterizing a patient, or new born, in proximately of an electrosurgical handpiece. When connector 190 is inserted into a radio frequency current generator, not shown, connector pins 160, 170, and 180 couple electrosurgical waveforms via cable 150 to handpiece 130. The surgical functions shown here as exemplars are "cut", selected via switch 135, or "coagulate", selected by switch 145 either of which when closed will provide a radio frequency electric field that will simultaneously ionize and illuminate internal gas indicator 125 and activate surgical blade 100.

In the event that a failure occurs in any part of the handpiece that causes an electric field to be present, in the handpiece, it will ionize internal gas indicator 125 visually annunciating its presence. Alternately, if the surgeon desires to test the handpiece he/she may select any mode of operation via pressing switches 135 or 145, without contacting the patient, and if the handpiece is operational internal gas indicator 125 will ionize and illuminate.

Figure 2:
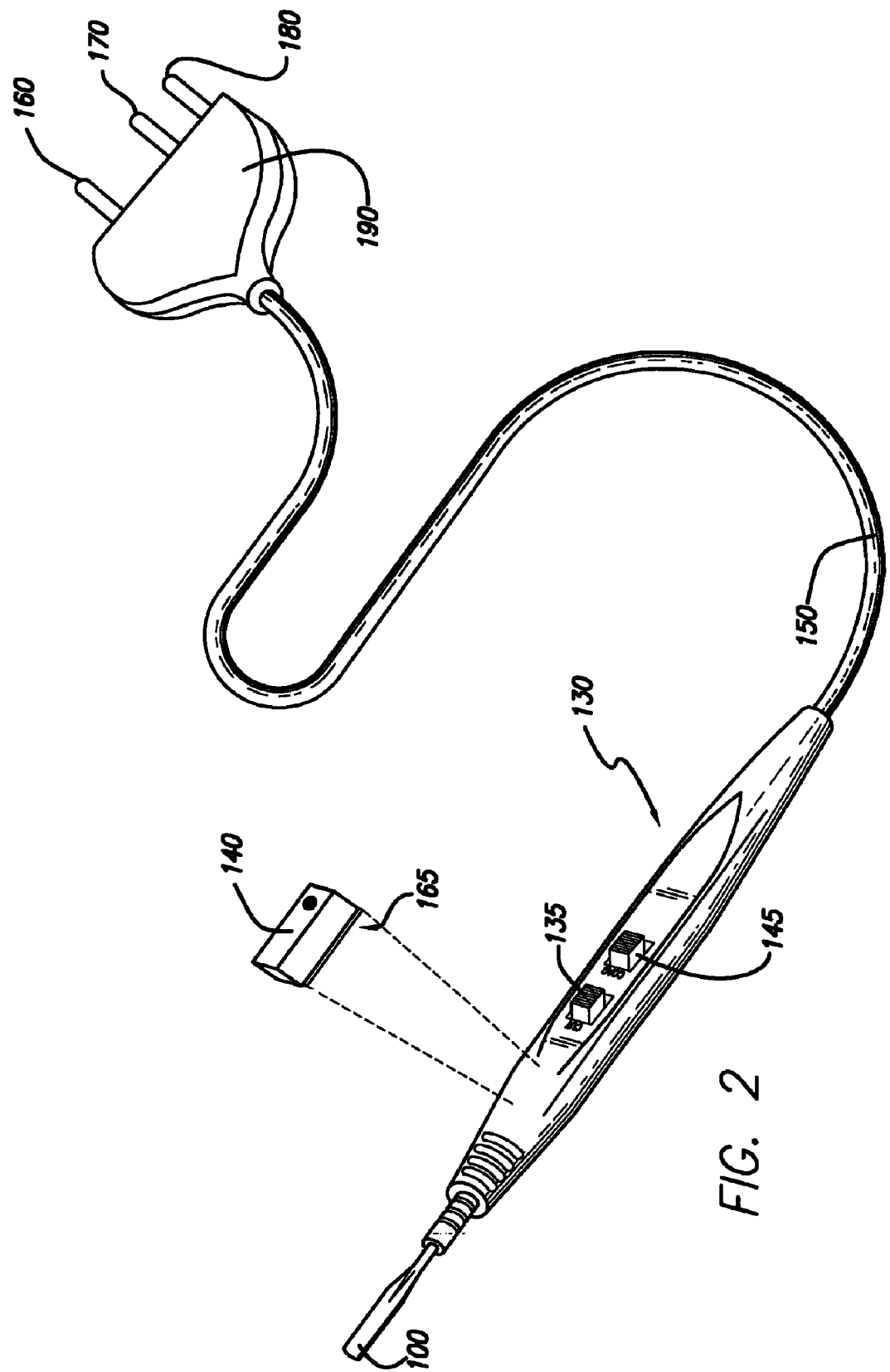
FIG. 2 is a pictorial of an accessory embodiment of the present invention to reduce the possibility of unintentionally cutting or cauterizing a patient, or new born, in proximately of an electrosurgical instrument.

FIG. 2 is an accessory embodiment of the present invention that can be applied to any surgical device and is functionally the same as the previously described above except that the visual gas indicator is housed in enclosure 140 and attached in an exemplary position to handpiece 130 as indicated via adhesive 165.

Figure 3:
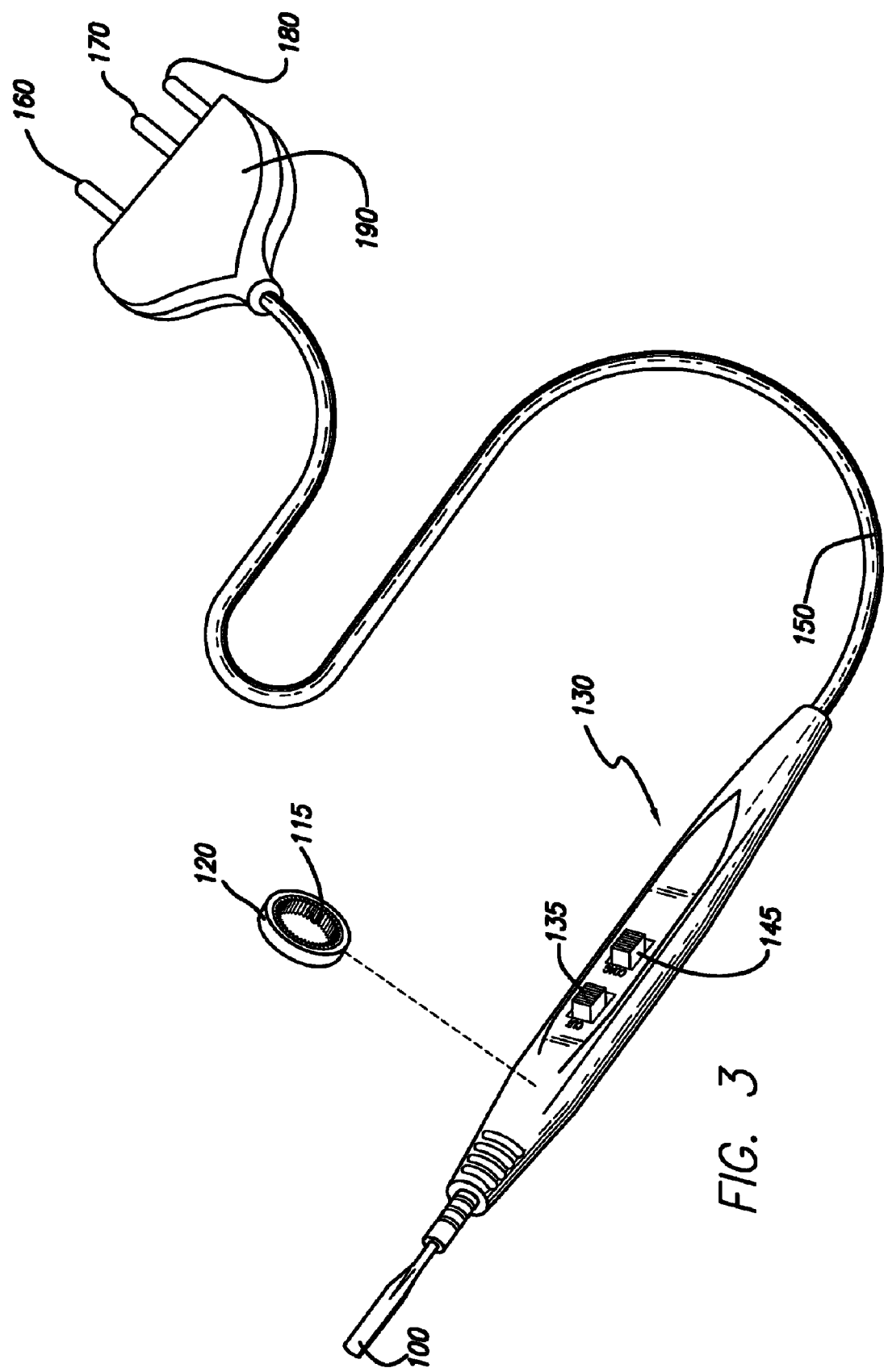
FIG. 3 is a pictorial of an alternate accessory embodiment of the present invention to reduce the possibility of unintentionally cutting or cauterizing a patient, or new born, in proximately of an electrosurgical instrument.

FIG. 3 is an alternate accessory embodiment of the present invention that is functionally the same as previously described except that the visual gas indicator 120 is circular and attached to handpiece 130 by grommet 115 by sliding grommet 115 over blade 100 into position indicated.

Some embodiments include a stand-alone visual indicator device that annunciates, without wiring or electrical contact with an object, whenever an electric field is present to reduce the possibility of unintentionally applying, or being in proximately of, radio frequency radiation with said device being comprised of: an electrically insulated enclosure filled with gas that illuminates in the presence of an electric field thereby avoiding accidents that can cause burns, lesions and other effects of electrostimulation.

In other embodiments, the visual indicator device as recited immediately above in paragraph, is further being integrated into a surgical device, such as a handpiece, that visually annunciates the presence of an electric field such that an observer knows that the surgical instrument is active and thereby avoid injury or unnecessary lesions to the patient.

In other embodiments, the visual indicator device as recited in paragraph, is further being encapsulated into an enclosure and applied to a surgical device, such as a handpiece, via an adhesive that visually annunciates the presence of an electric field such that an observer knows that the surgical instrument is active and thereby avoid injury or unnecessary lesions to the patient.

In other embodiments, the visual indicator device as recited in paragraph, is further being fabricated into a removable circular configuration with an accompanying grommet and applied to a surgical device, such as a handpiece, by forced fitting such that it visually annunciates the presence of an electric field from any perspective such that an observer knows that the surgical instrument is active and thereby avoid injury or unnecessary lesions to the patient.

In other embodiments, the visual indicator device as recited in paragraph, is further either by itself or being encapsulated into an enclosure and applied to, or in the presence of, an object in such a manner that when in the presence of an electric field the indicator illuminates alerting an observer of its presence.

In other embodiments, the visual indicator device as recited in paragraph, is further either by itself encapsulated into an enclosure, or interfaced to another object or device such that when in the presence of an electric field the indicator alerts the object or observer and causes an action.

In other embodiments, the visual indicator device as recited in paragraph, further includes either by itself or in communication with optical, infrared or other technology such that it may communicate with other control devices or indicator schemes.

In other embodiments, the visual indicator device as recited in paragraph, is in communication with computers, programmable logic controllers or other intelligent devices to reconstruct or process information either with or without the use of external communications or an external interface.

In other embodiments, the visual indicator device as recited in paragraph, is in communication with other electric field detection or process devices that are in communication with computers, programmable logic controllers or other intelligent devices to reconstruct or process information either with or without the use of external communications or an external interface.

It is readily apparent to those skilled in the art of medical equipment design and from reading the foregoing that many substitutions and modifications may be made to the preferred embodiments described without departing from the spirit and scope of the present invention.

What is claimed is:

1. A visual indicator for an electrosurgical device, comprising:
    an electrosurgical device having a handpiece having an electrically insulated cavity operably connected to said device;
    said electrically insulated cavity being filled with a gas;
    said electrosurgical device producing an electric field when active; and
    said gas producing light when said electrosurgical device is active.

2. The visual indicator device of claim 1, said electrically insulated cavity being housed in said electrosurgical device.

3. The visual indicator device of claim 1, said electrically insulated cavity being surrounded by an enclosure, said enclosure being attached to said electrosurgical device.

4. The visual indicator device of claim 3, said enclosure being attached via an adhesive to said electrosurgical device.

5. The visual indicator device of claim 1, said electrically insulated cavity having a circular configuration.

6. The visual indicator device of claim 5, said circular configuration being fitted with a grommet, said indicator being attached to said electrosurgical device via said grommet.

7. The visual indicator device of claim 1, said visual indicator device being connected directly or indirectly to another device.

8. The visual indicator device of claim 7, said indirect connection being via an infrared or other optical device such that it communicates with other control devices.

9. The visual indicator device of claim 1, said visual indicator device being in communication with a computer or programmable logic controller to provide a warning.

10. The visual indicator device of claim 1, said visual indicator device being connected to an electric field detection or process device, said electric field detection or process device being connected to a processor to provide a warning.

11. A surgical device comprising:
    an electrosurgical handpiece and a stand-alone visual indicator device that annunciates, without wiring or electrical contact with an object, whenever an electric field is present to reduce the possibility of unintentionally applying, or being in proximity of, radio frequency radiation with said device being comprised of:
    an electrically insulated enclosure filled with gas that illuminates in the presence of an electric field produced by the electrosurgical device, thereby avoiding accidents that can cause burns, lesions and other effects of electrostimulation, the visual indicator device further being fabricated into a removable circular configuration with an accompanying grommet and applied to the surgical device, such as the handpiece, by forced fitting such that it visually annunciates the presence of an electric field from any perspective such that an observer knows that the surgical instrument is active and thereby avoids injury or unnecessary lesions to the patient.

* * * * *